(12) United States Patent
Ma et al.

(10) Patent No.: US 7,838,703 B2
(45) Date of Patent: Nov. 23, 2010

(54) DIAROMATIC AMINE DERIVATIVES AS ANTIOXIDANTS

(75) Inventors: Qinggao Ma, Naugatuck, CT (US); Cyril Migdal, Pleasant Valley, NY (US)

(73) Assignee: Chemtura Corporation, Middlebury, CT (US)

( * ) Notice: Subject to any disclaimer, the term of this patent is extended or adjusted under 35 U.S.C. 154(b) by 516 days.

(21) Appl. No.: 11/941,806

(22) Filed: Nov. 16, 2007

(65) Prior Publication Data
US 2009/0131293 A1    May 21, 2009

(51) Int. Cl.
C07C 211/55    (2006.01)
C07D 221/18    (2006.01)
C10M 133/12    (2006.01)

(52) U.S. Cl. ................ 564/428; 546/61; 508/563; 508/261

(58) Field of Classification Search ........... 508/563, 508/261; 564/428; 546/61
See application file for complete search history.

(56) References Cited

U.S. PATENT DOCUMENTS

| | | | |
|---|---|---|---|
| 1,906,935 A | 5/1933 | Horst | |
| 1,975,167 A | 10/1934 | Meuser | |
| 2,002,642 A | 5/1935 | Meuser et al. | |
| 2,202,934 A | 6/1940 | Tuley et al. | |
| 2,562,802 A | 7/1951 | Mankowich et al. | |
| 2,650,252 A | 8/1953 | Mankowich | |
| 2,657,236 A | 10/1953 | Mankowich | |
| 2,660,605 A | 11/1953 | Newby | |
| 2,663,734 A | 12/1953 | Mankowich | |
| 2,666,792 A | 1/1954 | Mankowich | |
| 3,849,322 A | 11/1974 | Wendler et al. | |
| 5,213,699 A | 5/1993 | Babiarz et al. | |
| 5,268,394 A | 12/1993 | Wheeler et al. | |
| 6,613,917 B1 * | 9/2003 | Beard et al. | 549/23 |
| 2005/0230664 A1 | 10/2005 | Duyck et al. | |
| 2007/0155633 A1 | 7/2007 | Nalesnik | |
| 2007/0272894 A1 * | 11/2007 | Ma | 252/182.12 |

FOREIGN PATENT DOCUMENTS

| EP | 0538195 | 4/1993 |
|---|---|---|
| GB | 1 438 482 A | 6/1976 |
| JP | 10338658 A * | 12/1998 |

OTHER PUBLICATIONS

Chemical Abstract 754337, Oct. 2002, Japan.
Chemical Abstract 49839, Jan. 1959, US.
Chemical Abstract 545567, Jun. 1996, Japan.
Chemical Abstract 682342, Oct. 1998, Japan.
Chemical Abstract 713289, Sep. 2001, US.

* cited by examiner

Primary Examiner—Glenn A Caldarola
Assistant Examiner—Vishal Vasisth
(74) Attorney, Agent, or Firm—Joseph Suhadolnik

(57) ABSTRACT

A diaromatic amine compound having the general formula:

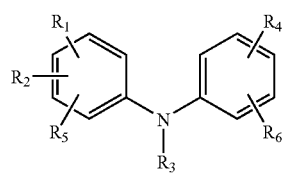

wherein $R_1$ and $R_2$ together with the carbon atoms to which they are bonded are joined together to form a $C_3$-$C_{30}$ ring, and $R_3$ is an allyl, benzyl, or methallyl group. $R_4$, $R_5$, and $R_6$ are independently hydrogen, $C_1$-$C_{30}$ alkyl group, $C_2$-$C_{30}$ alkenyl group, $C_3$-$C_{12}$ cycloalkyl group, $C_5$-$C_{25}$ aryl group, $C_6$-$C_{25}$ arylalkyl group, or $C_1$-$C_{30}$ alkoxy group.

18 Claims, No Drawings

DIAROMATIC AMINE DERIVATIVES AS ANTIOXIDANTS

BACKGROUND OF THE INVENTION

1. Field of the Invention

The present invention generally relates to additives for stabilizing organic products that are subjected to oxidative, thermal, and/or light-induced degradation. More particularly, the present invention relates to a class of diaromatic amine derivatives useful as antioxidants.

2. Description of Related Art

The stabilization of organic materials with antioxidants or other stabilizers is well known to those skilled in the art. For example, in developing lubricating oils, there have been many attempts to provide additives that impart, for example, antioxidant, antiwear, and deposit control properties thereto. Zinc dialkyldithiophosphates (ZDDPs) have been used as antifatigue, antiwear, antioxidant, extreme pressure and friction modifying additives for lubricating oils for many years. However, ZDDPs are subject to several drawbacks due to their zinc and phosphorus content. The presence of zinc, for example, contributes to the emission of zinc-containing particulates in the exhaust, which potentially presents toxicological and environmental issues. Also, when phosphorus-containing lubricating oil compositions are introduced into the combustion reaction of an engine, phosphorous enters the exhaust stream where it acts as a catalyst poison for catalytic converters. In this manner, phosphorous is suspected of limiting the service life of the catalytic converters that are used on cars to reduce pollution.

Thus, it is important to limit the formation of particulate matter and pollution during engine use for toxicological and environmental reasons, while maintaining the antioxidant properties of the lubricating oil.

It would therefore be desirable to provide improved additives for stabilizing organic products that are subject to oxidative, thermal, and/or light-induced degradation and in need of stabilization to prevent or inhibit such degradation, e.g., additives for lubricating oils that can improve the antioxidant properties of the oil.

SUMMARY

In a first aspect of the present invention there is provided a compound having the general formula I:

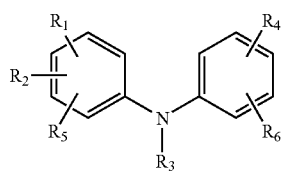

(I)

In this aspect, $R_1$ and $R_2$ together with the carbon atoms to which they are bonded are joined together to form a first $C_3$-$C_{30}$ ring. The first $C_3$-$C_{30}$ ring may be substituted with one or more substituents or may be unsubstituted. The first $C_3$-$C_{30}$ ring may contain one or more heteroatoms. The first $C_3$-$C_{30}$ ring may be saturated, partially unsaturated, or fully unsaturated. In various optional embodiments, $R_1$ and $R_2$ are joined to form a 5-, 6-, or 7-member ring.

In this aspect, $R_3$ is an allyl, a benzyl, or a methallyl group. $R_3$ together with the nitrogen to which is bonded may make the compound an electron withdrawing group.

In this aspect, $R_1$, $R_5$, and $R_6$ are each independently a substituent group. In one embodiment, $R_4$ and $R_6$ together with the carbon atoms to which they are bonded are joined together to form a second $C_3$-$C_{30}$ ring. The second $C_3$-$C_{30}$ ring may be substituted with one or more substituents or may be unsubstituted. The second $C_3$-$C_{30}$ ring may contain one or more heteroatoms. The second $C_3$-$C_{30}$ ring may be saturated, partially unsaturated, or fully unsaturated. In various optional embodiments, $R_4$ and $R_6$ are joined to form a 5-, 6-, or 7-member ring.

In a second aspect of the invention, the compounds of the present invention include those having the general formula II:

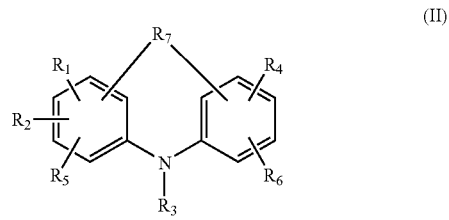

(II)

In this aspect, $R_1$, $R_2$, $R_3$, $R_4$, $R_5$, and $R_6$ are defined above. $R_7$ is $C_1$-$C_{30}$ alkyl group, $C_2$-$C_{30}$ alkenyl group, $C_3$-$C_{12}$ cycloalkyl group, $C_5$-$C_{25}$ aryl group, $C_6$-$C_{25}$ arylalkyl group, or $C_1$-$C_{30}$ alkoxy group. Each of these groups may be substituted with one or more substituents or may be unsubstituted. The $C_1$-$C_{30}$ alkyl group, $C_2$-$C_{30}$ alkenyl group, or $C_1$-$C_{30}$ alkoxy group may be branched or straight.

In a third aspect of the present invention there is provided lubricating oil composition comprising at least one oil of lubricating viscosity and an antioxidant improving effective amount of at least one compound having the general formula I or general formula II. The oil of lubricating viscosity may comprise engine oil, transmission fluid, hydraulic fluid, gear oil, marine cylinder oil, compressor oil, refrigeration lubricant or a mixture thereof. In one embodiment the lubricating oil composition further comprises at least one lubricating oil additive selected from the group consisting of antioxidants, anti-wear agents, detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and mixtures thereof. The lubricating oil additive preferably has a phosphorous content of less than about 0.1 weight percent, e.g., less than about 0.5 weight percent, or less than about 0.01 weight percent. In another embodiment, the lubricating oil composition further comprises a lubricating oil additive selected from the group consisting of an alkylated diphenylamine, alkylated hindered phenolic, alkylated substituted or unsubstituted phenylenediamine, alkylated oil soluble copper compound, alkylated sulfur containing compound known to impart oxidation stability and mixtures thereof. The alkylated sulfur containing compound known to impart oxidation stability preferably is selected from the group consisting of phenothiazines, sulfurized olefins, thiocarbamates, sulfur bearing hindered phenolics, zinc dialkyldithiophosphates and mixtures thereof.

In one embodiment, the lubricating oil composition has a thermo-oxidative engine oil stimulation test (TEOST) result for deposits that is less than 50 mg, e.g., less than 40 mg, less than 30 mg, or less than 20 mg.

In a fourth aspect of the present invention there is provided an additive package comprising from about 0.1 to about 75 weight percent, e.g., from about 0.5 to about 3 weight percent, or from about 1 to about 2 weight percent, of at least one compound of having the general formula I or formula II.

In a fifth aspect of the present invention there is provided a stabilizer-containing composition comprising an organic material subject to oxidative, thermal, and/or light-induced degradation and in need of stabilization to prevent or inhibit such degradation, and a stabilization effective amount of at least one compound having the general formula I or formula II.

In a sixth aspect of the present invention there is provided a method for stabilizing an organic material subject to oxidative, thermal, and/or light-induced degradation and in need of stabilization to prevent or inhibit such degradation, the method comprising adding to the organic material a stabilizing amount of at least one compound having the general formula I or II.

In a seventh aspect of the present invention there is provided a compound comprising a diaromatic amine having at least two phenyl groups bonded to a nitrogen, wherein the nitrogen is further bonded to a carbon containing substituent group such that the compound is an capable of being an electron withdrawing group; and a first ring fused to one of the phenyl groups.

DESCRIPTION OF THE INVENTION

The present invention, in one embodiment, is directed to a class of diaromatic amine derivatives having the general formula I:

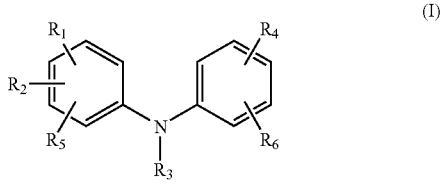

In this embodiment, $R_1$ and $R_2$ together with the carbon atoms to which they are bonded are joined together to form a first $C_3$-$C_{30}$ ring. The first $C_3$-$C_{30}$ ring is fused to one of the phenyl groups shown in formula I. By "fused" it is meant that the ring shares at least two or more carbon atoms of a phenyl group shown in formula I. The first $C_3$-$C_{30}$ ring may be substituted with one or more substituents or may be unsubstituted. The first $C_3$-$C_{30}$ ring may contain one or more heteroatoms. The first $C_3$-$C_{30}$ ring may be saturated, partially unsaturated, or fully unsaturated. The first $C_3$-$C_{30}$ ring may be a cycloalkyl group, cycloalkenyl group or an aryl group. In various optional embodiments, the ring comprises $C_3$-$C_{18}$ cycloalkyl group, and more preferably $C_4$-$C_9$ cycloalkyl group.

In this embodiment, $R_3$ may be allyl, benzyl, methallyl group, etc., or a substituent thereof. $R_3$ together with the nitrogen to which it is bonded may make the compound capable of being an electron withdrawing group (EWG). As used herein EWG refers to the group's ability to draws electrons away from a reaction center. In some optional embodiments, $R_3$ may be an EWG such as a weakly activating EWG including halides, mild activating EWG including carboxylic acids, carbonyls, other carbon containing substituents, etc., or strongly activating EWG such as nitriles, sulfonates, other carbon containing substituents, etc.

In this embodiment, $R_4$, $R_5$, and $R_6$ are independently hydrogen, $C_1$-$C_{30}$ alkyl group, $C_2$-$C_{30}$ alkenyl group, $C_3$-$C_{12}$ cycloalkyl group, $C_5$-$C_{25}$ aryl group, $C_6$-$C_{25}$ arylalkyl group, or $C_1$-$C_{30}$ alkoxy group. Each of these groups may be substituted with one or more substituents or may be unsubstituted. The $C_1$-$C_{30}$ alkyl group, $C_2$-$C_{30}$ alkenyl group, or $C_1$-$C_{30}$ alkoxy group may be branched or straight.

Preferably the alkyl group comprises $C_3$-$C_{20}$, and more preferably $C_4$-$C_{14}$. Preferably the alkenyl group comprises $C_3$-$C_{20}$, and more preferably $C_4$-$C_{14}$. Preferably the cycloalkyl group comprises $C_4$-$C_{10}$, and more preferably $C_5$-$C_8$. Preferably the aryl group comprises $C_5$-$C_{15}$, and more preferably $C_6$-$C_{10}$. Preferably the arylalkyl group comprises $C_4$-$C_{15}$, and more preferably $C_5$-$C_8$. Preferably the alkoxy group comprises $C_3$-$C_{20}$, and more preferably $C_4$-$C_{14}$.

In one embodiment, $R_4$ and $R_6$ together with the carbon atoms to which they are bonded are joined together to form a second $C_3$-$C_{30}$ ring. The second $C_3$-$C_{30}$ ring is fused to one of the phenyl groups shown in formula I. The second $C_3$-$C_{30}$ ring may be substituted with one or more substituents or may be unsubstituted. The second $C_3$-$C_{30}$ ring may contain one or more heteroatoms. The second $C_3$-$C_{30}$ ring may be saturated, partially unsaturated, or fully unsaturated. The second $C_3$-$C_{30}$ ring is a cycloalkyl group, cycloalkenyl group, or an aryl group. Preferably the ring comprises $C_3$-$C_{18}$ cycloalkyl group, and more preferably $C_4$-$C_9$ cycloalkyl group.

Representative examples of alkyl groups for use herein for $R_4$, $R_5$, $R_6$ and $R_7$ include, for example, a straight or branched hydrocarbon chain radical containing from 1 to 30 carbon atoms, e.g., methyl, ethyl, n-propyl, 1-methylethyl (isopropyl), n-butyl, n-pentyl, etc., mixtures and isomers thereof, and the like.

Representative examples of alkenyl groups for use herein for $R_4$, $R_5$, $R_6$ and $R_7$ include, for example, a straight or branched hydrocarbon chain radical containing from 2 to 30 carbon atoms, e.g., ethenyl, propenyl, butenyl, pentenyl, hexenyl, etc., mixtures and isomers thereof, and the like. The alkenyl group may have one or more double bonds and may include dialkenyl groups, trialkenyl groups, tetraalkenyl groups, etc.

Representative examples of cycloalkyl groups for use herein for $R_4$, $R_5$, $R_6$ and $R_7$ include, for example, a ring containing from 2 to 12 carbon atoms, e.g., cyclopropyl, cyclobutyl, cyclopentyl, cyclohexyl, etc., mixtures and isomers thereof, and the like. The rings may be unsubstituted or substituted with one or more substituents and/or contain one or more heteroatoms.

Representative examples of cycloalkyl groups for use herein for the joined ring containing from 3 to 30 carbon atoms for $R_1$ and $R_2$ or the optional joined ring containing from 3 to 30 carbon atoms for $R_4$ and $R_6$, include, for example, cyclopropyl, cyclobutyl, cyclopentyl, cyclohexyl, cycloheptyl, etc., mixtures thereof, and the like. The rings may be unsubstituted or may be substituted with one or more substituents and/or contain one or more heteroatoms.

Representative examples of cycloalkenyl groups for use herein for the joined ring containing from 3 to 30 carbon atoms for $R_1$ and $R_2$ or the optional joined ring containing from 3 to 30 carbon atoms for $R_4$ and $R_6$, include, for example, cyclopropenyl, cyclobutenyl, cyclopentenyl, cyclohexenyl, cycloheptenyl, etc., mixtures and thereof, and the like. The rings may be unsubstituted or may be substituted with one or more substituents and/or contain one or more heteroatoms. The cycloalkenyl group may have one or more double bonds and may include cyclodialkenyl groups, cyclotrialkenyl groups, cyclotetraalkenyl groups, etc.

Representative examples of aryl groups for use herein for $R_4$, $R_5$, and $R_6$ include, for example, aromatic rings containing from 5 to 25 carbon atoms, e.g., phenyl, naphthyl, tetrahydronapthyl, indenyl, biphenyl, etc., mixtures and thereof, and the like. The rings may be unsubstituted or may be substituted with one or more substituents and/or contain one or more heteroatoms.

Representative examples of aryl groups for use herein for the joined ring containing from 3 to 30 carbon atoms for $R_1$ and $R_2$ or the optional joined ring containing from 3 to 30 carbon atoms for $R_4$ and $R_6$, include, for example, phenyl, naphthyl, tetrahydronapthyl, indenyl, biphenyl, etc., mixtures and thereof, and the like. The rings may be unsubstituted or may be substituted with one or more substituents and/or contain one or more heteroatoms.

Representative examples of arylalkyl groups for use herein for $R_4$, $R_5$, and $R_6$ include, for example, aromatic rings having an alkyl group that contain from 6 to 25 carbon atoms, e.g., methylphenyl, n,n-dimethylphenyl, ethylphenyl, propylphenyl, etc., mixtures and thereof, and the like. The rings may be unsubstituted or may be substituted with one or more substituents and/or contain one or more heteroatoms.

Representative examples of alkoxy groups for use herein for $R_4$, $R_5$, $R_6$ and $R_7$ include, for example, a straight or branched hydrocarbon chain radical having an oxy group and containing from 1 to 30 carbon atoms, e.g., methoxy, ethoxy, propoxy, butoxy, pentoxy, etc., mixtures and isomers thereof, and the like.

Where any of $R_1$, $R_2$, $R_3$, $R_4$, $R_5$, $R_6$ and $R_7$ are substituted or are substituents, representative examples of substituents may include hydrogen, hydroxy, halogen, carboxyl, cyano, nitro, oxo (=O), thio(=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted or unsubstituted heterocycloalkyl ring, substituted or unsubstituted heteroarylalkyl, substituted or unsubstituted heterocyclic ring, —$R_xOH$, —$R_xHO$, —$COOR_x$, —$C(O)R_x$, —$C(S)R_x$, —$C(O)NR_xR_y$, —$C(O)ONR_xR_y$, —$NR_xCONR_yR_z$, —$N(R_x)SOR_y$, —$N(R_x)SO2R_y$, —(=N—N(R_x)R_y), —$NR_xC(O)OR_y$, —$NR_xR_y$, —$NR_xC(O)R_y$, —$NR_xC(S)R_y$, —$NR_xC(S)NR_yR_z$, —$SONR_xR_y$, —$SO2NR_xR_y$, —$OR_x$, —$OR_xC(O)NR_yR_z$, —$OR_xC(O)OR_y$, —$OC(O)R_x$, —$OC(O)NR_xR_y$, —$R_xNR_yC(O)R_z$, —$R_xOR_y$, —$R_xC(O)OR_y$, —$R_xC(O)NR_yR_z$, —$R_xC(O)R_x$, —$R_xOC(O)R_y$, —$SR_x$, —$SOR_x$, —$SO_2R_x$, —$ONO_2$, wherein $R_x$, $R_y$, and $R_z$ in each comprising a saturated or unsaturated chain of 1 to 30 carbons.

Where any of $R_1$, $R_2$, $R_3$, $R_4$, $R_5$, and $R_6$ contain one or more heteroatoms, those heteroatoms may be N, O, S, and the like.

In one embodiment, compounds of the present invention include those having the general formula II:

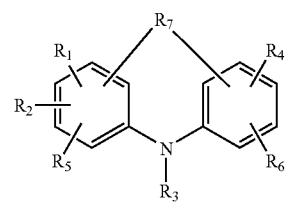

(II)

In this embodiment, $R_1$, $R_2$, $R_3$, $R_4$, $R_5$, and $R_6$ are defined above. $R_7$ may be $C_1$-$C_{30}$ alkyl group, $C_2$-$C_{30}$ alkenyl group, $C_3$-$C_{12}$ cycloalkyl group, $C_5$-$C_{25}$ aryl group, $C_6$-$C_{25}$ arylalkyl group, or $C_1$-$C_{30}$ alkoxy group. Each of these groups may be substituted with one or more substituents or may be unsubstituted. The $C_1$-$C_{30}$ alkyl group, $C_2$-$C_{30}$ alkenyl group, or $C_1$-$C_{30}$ alkoxy group may be branched or straight.

In another embodiment, compounds of the present invention include those having the general formula III:

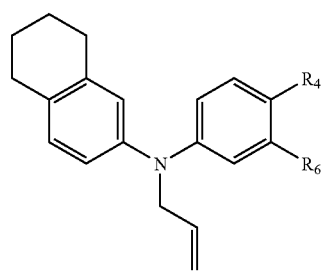

(III)

In this embodiment, with reference to formula I, $R_1$ and $R_2$ are joined to for a saturated 6-membered ring, which is fused to one of the phenyl groups. In this context, by saturated it is meant that the $R_1$ and $R_2$ groups are saturated, but not the bond shared between the 6-membered ring and the fused phenyl group. In this embodiment, $R_3$ is an allyl group, $R_5$ is a hydrogen, and $R_4$ and $R_6$ are defined above.

In another embodiment, compounds of the present invention include those having the general formula IV:

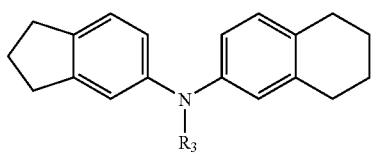

(IV)

In this embodiment, with reference to formula I, $R_1$ and $R_2$ are joined to form a saturated 5-membered ring, which is fused to one of the phenyl groups. In this embodiment, $R_4$ and $R_6$ are joined to form a saturated 6-membered ring, which is fused to the other phenyl group, $R_5$ is a hydrogen, and $R_3$ is defined above.

In another embodiment, compounds of the present invention include those having the general formula V:

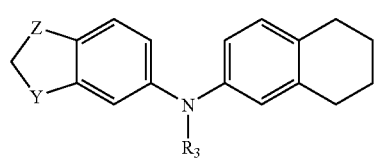

(V)

In this embodiment, with reference to formula I, $R_1$ and $R_2$ are joined to form a saturated 5-membered ring, which is fused to one of the phenyl groups. Y and Z represent heteroatoms, such as, for example, N, O, and S. In this embodiment, $R_4$ and $R_6$ are joined to form a saturated 6-membered ring, which is fused to the other phenyl group, $R_5$ is a hydrogen, and $R_3$ is defined above.

In another embodiment, compounds of the present invention include those having the general formula VI:

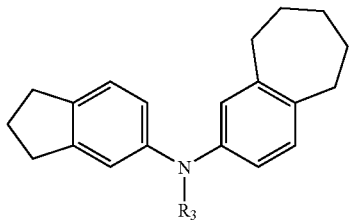
(VI)

In this embodiment, with reference to formula (I), $R_1$ and $R_2$ are joined to form a saturated 5-membered ring, which is fused to one of the phenyl groups. $R_4$ and $R_6$ are joined to form a saturated 7-membered ring, which is fused to the other phenyl group. In this embodiment, $R_5$ is hydrogen, and $R_3$ is defined above.

In another embodiment, compounds of the present invention include those having the general formula VII:

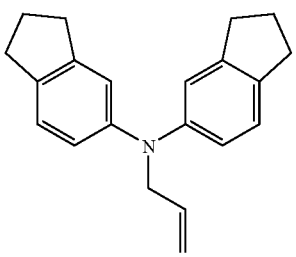
(VII)

In this embodiment, with reference to formula I, $R_1$ and $R_2$ are joined to form a saturated 5-membered ring, which is fused to one of the phenyl groups. $R_4$ and $R_6$ are joined to form a saturated 5-membered ring, which is fused to the other phenyl group. In this embodiment, $R_3$ is an allyl group, and $R_5$ is hydrogen.

In another embodiment, compounds of the present invention include those having the general formula VIII:

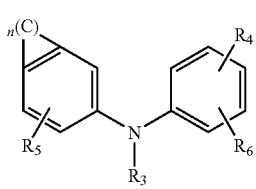
(VIII)

In this embodiment, with reference to formula I, $R_1$ and $R_2$ are joined and n is from 1 to 9, e.g., 2 to 7, or 3 to 5, to form a saturated or partially saturated 3-, 4-, 5-, 6-, 7-, 8-, 9-, 10- or 11-membered ring, which is fused to one of the phenyl groups. $R_3$, $R_4$, $R_5$, and $R_6$ are defined above, with the provision that $R_4$ and $R_6$ are not joined.

In one embodiment, the foregoing diaromatic amine derivatives may be derived by reacting an amino compound of general formula IX, a halide aryl compound of general formula X, and a halide electron withdrawing group compound of general formula XI in the presence of one or more catalysts:

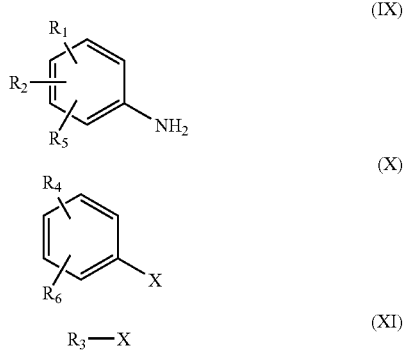

In this reaction, $R_1$, $R_2$, $R_3$, $R_4$, $R_5$, and $R_6$ are defined above. X is a halide. Useful halides include, but are not limited to, bromine, chlorine, iodine, and fluorine.

The diaromatic amine derivatives of the present invention can be obtained by reacting the amino compound of the formula IX and the halide aryl of formula X in the presence of a suitable catalyst. Useful catalysts include, but are not limited to, palladium-containing catalysts, copper-containing catalysts and the like and mixtures thereof. Suitable palladium-containing catalysts include, but are not limited to, tetrakis(triphenylphosphine)palladium, (dibenzylideneacetone)palladium, (dibenzylideneacetate)palladium, (tris (dibenzylideneacetate)dipalladium, bis(tricyclohexylphosphine)palladium, (2-(diphenylphosphino)ethyl)palladium, palladium(0) bis-(tri-t-butylphoshine), (1,1'-bis(diphenylphosphino)ferrocene)palladium, bis(triphenylphosphine) dichloropalladium, bis(1,1'-bis(diphenylphosphino) ferrocene)palladium, bis(2-(diphenylphosphino)ethyl) dichloropalladium, $PdCl_2$ $(CH_3CN)_2$ and the like. Suitable copper-containing catalysts include, but are not limited to, $Cu(PPh_3)_3Br$, $CuPPh_3$ (phenantholine) Br, $CuPPh_3$ (1,10-dimethyl phenantholine) Br and the like. The catalyst preferably is present in an amount sufficient to promote the reaction. For example, in one embodiment, a copper-containing catalyst is employed and is present in the reaction in an amount ordinarily ranging from about 15 to about 25 wt. %, based on the total weight of the reactants (with no solvent). In another embodiment, a palladium-containing catalyst is employed and is present in the reaction in an amount ordinarily ranging from about 0.5 to about 5%, e.g., from about 1 to about 3 wt. %, based on the total weight of the reactants (with no solvent).

The catalyst may be used in the form of a fixed bed in the reactor or, for example, in the form of a fluidized bed and can have an appropriate shape. Suitable shapes include, for example, granules, pellets, monoliths, spheres or extrudates.

The reaction of compounds IX and X is advantageously conducted under an inert gas atmosphere such as argon or nitrogen. The temperature for this reaction will ordinarily range from about 80° C. to about 150° C. and more preferably from about 95° C. to about 105° C. Generally, the molar ratio of the amino compound of the formula IX to the halide aryl of formula X can range from about 0.9:1 to about 1:0.9 and preferably from about 0.95:1 to about 1:0.95.

The reaction of compounds IX and X may be carried in one or more solvents, including diethyl ethylene glycol, toluene, alcohols, acetones, methyl ethyl ketone, trichloroethane, and xylene.

The product of the reaction between compounds IX and X preferably is further reacted with compound XI in the presence of a solvent, and under ambient temperature and pressure conditions. Suitable solvents include polar aprotic solvents such as dimethyl sulfoxide (DMSO), dimethylformamide (DMF), and hexamethylphosphorotriamide (HMPA).

In this process of the present invention, the reaction may be carried out in the presence of one or more bases. Suitable bases include potassium carbonate, sodium carbonate, sodium bicarbonate, etc.

The diaromatic amine derivatives or an isomer or isomeric mixture thereof of this invention may be used as a stabilizer in a stabilizer-containing composition containing an organic material subject to oxidative, thermal, and/or light-induced degradation and in need of stabilization to prevent or inhibit such degradation. Illustrative examples of such organic materials are as follows:

1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultra-high molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e., the polymers of monoolefins exemplified in the preceding paragraph, preferably polyethylene and polypropylene, and can be prepared by different, and especially by the following, methods: (a) radical polymerisation (normally under high pressure and at elevated temperature; or (b) catalytic polymerisation using a catalyst that normally contains one or more than one metal of Groups IVb, Vb, VIb or VIII of the Periodic Table. These metals usually have one or more than one ligand, typically oxides, halides, alcoholates, esters, ethers, amines, alkyls, alkenyls and/or aryls that may be either pi- or sigma-coordinated. These metal complexes may be in the free form or fixed on substrates, typically on activated magnesium chloride, titanium (III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of Groups Ia, IIa and/or IIIa of the Periodic Table. The activators may be modified conveniently with further ester, ether, amine or silyl ether groups. These catalyst systems are usually termed Phillips, Standard Oil Indiana, Ziegler (Natta), TNZ (DuPont), metallocene or single site catalysts (SSC).

2. Mixtures of the polymers mentioned under (1), for example, mixtures of polypropylene with polyIsobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example, ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in (1) above, for example, polypropylene/ethylene-propylene copolymers, LDPE/ethylene-vinyl acetate copolymers (EVA), LDPE/ethylene-acrylic acid copolymers (EM), LLDPE/EVA, LLDPE/EAA and alternating or random polyalkylene/carbon monoxide copolymers and mixtures thereof with other polymers, for example, polyamides.

4. Hydrocarbon resins (for example $C_5$-$C_9$) including hydrogenated modifications thereof (e.g., tackifiers) and mixtures of polyalkylenes and starch.

Homopolymers and copolymers from 1.)-4.) may have any stereostructure including syndiotactic, isotactic, hemi-isotactic or atactic; where atactic polymers are preferred. Stereoblock polymers are also included.

5. Polystyrene, poly(p-methylstyrene), poly($\alpha$-methylstyrene).

6. Aromatic homopolymers and copolymers derived from vinyl aromatic monomers including styrene, $\alpha$-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including the aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, e.g., a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under (6), including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under (6a).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or $\alpha$-methylstyrene, e.g., styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under (6), for example, the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfo-chlorinated polyethylene, copolymers of ethylene and chlorinated ethylene, epichlorohydrin homo- and copolymers, especially polymers of halogen-containing vinyl compounds, for example, polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under (9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in (1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example, polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example, poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g., with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example, polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g., products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose.

28. Blends of the aforementioned polymers (polyblends), for example, PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

29. Naturally occurring and synthetic organic materials which are pure monomeric compounds or mixtures of such compounds, for example, mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

Preferred organic materials are natural, semi-synthetic and synthetic polymers as described above. Representative examples of such organic materials for use herein include polyols, urethanes, reaction products of polyols and urethanes, plastics, greases, roof sheeting, motor oils, cables, gaskets, seals, rubber-containing compositions such as compounded tires, rubber belts, cables, gaskets, seals and rubber products in the garment and carpet industries.

The diaromatic amine derivatives of the present invention can be added to the organic material in an amount sufficient to impart an appreciable stabilizing effect. In general, this amount may vary from about 0.1 wt. % to about 5 wt. %, preferably from about 0.5 wt. % to about 3 wt. % and more preferably from about 0.5 wt. % to about 2.0 wt. %, by total weight of the organic material. The diaromatic amine derivatives can be incorporated into the organic material by conventional methods, for example, in any desired phase during the manufacture of shaped products. They can, for example, be mixed in the form of a liquid, a paste, a powder with other materials, suspensions or emulsions or solutions into the polymer, which can be in the form of a powder, melt, solution, suspension or emulsion.

Another embodiment of the present invention is a lubricating oil composition containing at least (a) an oil of lubricating viscosity and (b) an effective amount of at least one of the diaromatic amine derivatives or an isomer or isomeric mixture thereof of this invention. Generally, the oil of lubricating viscosity for use in the lubricating oil compositions may be present in a major amount, e.g., an amount of greater than 50 wt. %, preferably greater than about 70 wt. %, more preferably from about 80 to about 99.5 wt. % and most preferably from about 85 to about 98 wt. %, based on the total weight of the composition. The diaromatic amine derivatives of this invention can be added to the lubricating oil composition in an effective amount ranging from about 0.1 wt. % to about 75 wt. %, preferably 0.1 wt. % to about 10 wt. %, preferably from about 0.5 wt. % to about 3 wt. % weight percent and more preferably from about 1 wt. % to about 2 wt. %, based on the total weight of the lubricating oil composition.

The oil of lubricating viscosity for use herein can be any presently known or later-discovered oil of lubricating viscosity used in formulating lubricating oil compositions for any and all such applications, e.g., engine oils, marine cylinder oils, functional fluids such as hydraulic oils, gear oils, transmission fluids, e.g., automatic transmission fluids, etc., turbine lubricants, compressor lubricants, metal-working lubricants, and other lubricating oil and grease compositions. Additionally, the oil of lubricating viscosity for use herein can optionally contain viscosity index improvers, e.g., polymeric alkylmethacrylates; olefinic copolymers, e.g., an ethylene-propylene copolymer or a styrene-butadiene copolymer; and the like and mixtures thereof.

As one skilled in the art would readily appreciate, the viscosity of the oil of lubricating viscosity is dependent upon the application. Accordingly, the viscosity of an oil of lubricating viscosity for use herein will ordinarily range from about 2 to about 2000 centistokes (cSt) at 100° C. Generally, individually the oils used as engine oils will have a kinematic viscosity range at 100° C. of about 2 cSt to about 30 cSt, preferably about 3 cSt to about 16 cSt, and most preferably about 4 cSt to about 12 cSt and will be selected or blended depending on the desired end use and the additives in the finished oil to give the desired grade of engine oil, e.g., a lubricating oil composition having an SAE Viscosity Grade of 0W, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20, 15W-30 or 15W-40. Oils used as gear oils can have viscosities ranging from about 2 cSt to about 2000 cSt at 100° C.

Base stocks may be manufactured using a variety of different processes including, but not limited to, distillation, solvent refining, hydrogen processing, oligomerization, esterification, and rerefining. Rerefined stock shall be substantially free from materials introduced through manufacturing, contamination, or previous use. The base oil of the lubricating oil compositions of this invention may be any natural or synthetic lubricating base oil. Suitable hydrocarbon synthetic oils include, but are not limited to, oils prepared from the polymerization of ethylene or from the polymerization of 1-olefins to provide polymers such as polyalphaolefin or PAO oils, or from hydrocarbon synthesis procedures using carbon monoxide and hydrogen gases such as in a Fisher-Tropsch process. For example, a suitable oil of lubricating viscosity is one that comprises little, if any, heavy fraction; e.g., little, if any, lube oil fraction of viscosity about 20 cSt or higher at 100° C.

The oil of lubricating viscosity may be derived from natural lubricating oils, synthetic lubricating oils or mixtures thereof. Suitable oils includes base stocks obtained by isomerization of synthetic wax and slack wax, as well as hydrocracked base stocks produced by hydrocracking (rather than solvent extracting) the aromatic and polar components of the crude. Suitable oils include those in all API categories I, II, III, IV and V as defined in API Publication 1509, 14th Edition, Addendum I, December 1998. Group IV base oils are polyalphaolefins (PAO). Group V base oils include all other base oils not included in Group I, II, III, or IV. Although Group II, III and IV base oils are preferred for use in this invention, these preferred base oils may be prepared by combining one or more of Group I, II, III, IV and V base stocks or base oils.

Useful natural oils include mineral lubricating oils such as, for example, liquid petroleum oils, solvent-treated or acid-treated mineral lubricating oils of the paraffinic, naphthenic or mixed paraffinic-naphthenic types, oils derived from coal or shale, animal oils, vegetable oils (e.g., rapeseed oils, castor oils and lard oil), and the like.

Useful synthetic lubricating oils include, but are not limited to, hydrocarbon oils and halo-substituted hydrocarbon oils such as polymerized and interpolymerized olefins, e.g., polybutylenes, polypropylenes, propylene-isobutylene copolymers, chlorinated polybutylenes, poly(1-hexenes), poly(1-octenes), poly(1-decenes), and the like and mixtures thereof; alkylbenzenes such as dodecylbenzenes, tetradecylbenzenes, dinonylbenzenes, di(2-ethylhexyl)-benzenes, and the like; polyphenyls such as biphenyls, terphenyls, alkylated polyphenyls, and the like; alkylated diphenyl ethers and alkylated diphenyl sulfides and the derivative, analogs and homologs thereof and the like.

Other useful synthetic lubricating oils include, but are not limited to, oils made by polymerizing olefins of less than 5 carbon atoms such as ethylene, propylene, butylenes, isobutene, pentene, and mixtures thereof. Methods of preparing such polymer oils are well known to those skilled in the art.

Additional useful synthetic hydrocarbon oils include liquid polymers of alpha olefins having the proper viscosity. Especially useful synthetic hydrocarbon oils are the hydrogenated liquid oligomers of $C_6$ to $C_{12}$ alpha olefins such as, for example, 1-decene trimer.

Another class of useful synthetic lubricating oils includes, but is not limited to, alkylene oxide polymers, i.e., homopolymers, interpolymers, and derivatives thereof where the terminal hydroxyl groups have been modified by, for example, esterification or etherification. These oils are exemplified by the oils prepared through polymerization of ethylene oxide or propylene oxide, the alkyl and phenyl ethers of these polyoxyalkylene polymers (e.g., methyl poly propylene glycol ether having an average molecular weight of about 1,000, diphenyl ether of polyethylene glycol having a molecular weight of about 500 to about 1000, diethyl ether of polypropylene glycol having a molecular weight of about 1,000 to about 1,500, etc.) or mono- and polycarboxylic esters thereof such as, for example, the acetic esters, mixed $C_3$-$C_8$ fatty acid esters, or the $C_{13}$oxo acid diester of tetraethylene glycol.

Yet another class of useful synthetic lubricating oils include, but are not limited to, the esters of dicarboxylic acids e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acids, alkyl malonic acids, alkenyl malonic acids, etc., with a variety of alcohols, e.g., butyl alcohol, hexyl alcohol, dodecyl alcohol, 2-ethylhexyl alcohol, ethylene glycol, diethylene glycol monoether, propylene glycol, etc. Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include, but are not limited to, those made from carboxylic acids having from about 5 to about 12 carbon atoms with alcohols, e.g., methanol, ethanol, etc., polyols and polyol ethers such as neopentyl glycol, trimethylol propane, pentaerythritol, dipentaerythritol, tripentaerythritol, and the like.

Silicon-based oils such as, for example, polyalkyl-, polyaryl-, polyalkoxy- or polyaryloxy-siloxane oils and silicate oils, comprise another useful class of synthetic lubricating oils. Specific examples of these include, but are not limited to, tetraethyl silicate, tetra-isopropyl silicate, tetra-(2-ethylhexyl) silicate, tetra-(4-methyl-hexyl)silicate, tetra-(p-tert-butylphenyl)silicate, hexyl-(4-methyl-2-pentoxy)disiloxane, poly(methyl)siloxanes, poly(methylphenyl)siloxanes, and the like. Still yet other useful synthetic lubricating oils include, but are not limited to, liquid esters of phosphorous containing acids, e.g., tricresyl phosphate, trioctyl phosphate, diethyl ester of decane phosphonic acid, etc., polymeric tetrahydrofurans and the like.

The oil of lubricating viscosity may be derived from unrefined, refined and rerefined oils, either natural, synthetic or mixtures of two or more of any of these of the type disclosed hereinabove. Unrefined oils are those obtained directly from a natural or synthetic source (e.g., coal, shale, or tar sands bitumen) without further purification or treatment. Examples of unrefined oils include, but are not limited to, a shale oil obtained directly from retorting operations, a petroleum oil obtained directly from distillation or an ester oil obtained directly from an esterification process, each of which is then used without further treatment. Refined oils are similar to the unrefined oils except they have been further treated in one or more purification steps to improve one or more properties. These purification techniques are known to those of skill in the art and include, for example, solvent extractions, secondary distillation, acid or base extraction, filtration, percolation, hydrotreating, dewaxing, etc. Rerefined oils are obtained by treating used oils in processes similar to those used to obtain refined oils. Such rerefined oils are also known as reclaimed or reprocessed oils and often are additionally processed by techniques directed to removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst.

Natural waxes are typically the slack waxes recovered by the solvent dewaxing of mineral oils; synthetic waxes are typically the wax produced by the Fischer-Tropsch process.

The diaromatic amine derivatives or isomer or isomeric mixture thereof of this invention can be used as a complete or partial replacement for commercially available antioxidants currently used in lubricant formulations and can be in combination with other additives typically found in motor oils and fuels. When used in combination with other types of antioxidants or additives used in oil formulations, synergistic and/or additive performance effects may also be obtained with respect to improved antioxidancy, antiwear, frictional and detergency and high temperature engine deposit properties. Such other additives can be any presently known or later-discovered additives used in formulating lubricating oil compositions. The lubricating oil additives typically found in lubricating oils are, for example, dispersants, detergents, corrosion/rust inhibitors, antioxidants, anti-wear agents, antifoamants, friction modifiers, seal swell agents, emulsifiers, VI improvers, pour point depressants, and the like. See, for example, U.S. Pat. No. 5,498,809 for a description of useful lubricating oil composition additives, the disclosure of which is incorporated herein by reference in its entirety.

Examples of dispersants include polyisobutylene succinimides, polyisobutylene succinate esters, Mannich Base ashless dispersants, and the like. Examples of detergents include metallic and ashless alkyl phenates, metallic and ashless sulfurized alkyl phenates, metallic and ashless alkyl sulfonates, metallic and ashless alkyl salicylates, metallic and ashless saligenin derivatives, and the like.

Examples of other antioxidants include alkylated diphenylamines, N-alkylated phenylenediamines, phenyl-naphthylamine, alkylated phenyl-naphthylamine, dimethyl quinolines, trimethyldihydroquinolines and oligomeric compositions derived therefrom, hindered phenolics, alkylated hydroquinones, hydroxylated thiodiphenyl ethers, alkylidenebisphenols, thiopropionates, metallic dithiocarbamates, 1,3,4-dimercaptothiadiazole and derivatives, oil soluble copper compounds, and the like. Representative examples of such additives are those commercially available from such sources as Chemtura Corporation and include, for example, Naugalube® 438, Naugalube 438L, Naugalube 640, Naugalube 635, Naugalube 680, Naugalube AMS, Naugalube APAN, Naugard PANA, Naugalube TMQ, Naugalube 531, Naugalube 431, Naugard® BHT, Naugalube 403, Naugalube 420 and the like.

Examples of anti-wear additives that can be used in combination with the additives of the present invention include organo borates, organo phosphites, organo phosphates, organic sulfur-containing compounds, sulfurized olefins, sulfurized fatty acid derivatives (esters), chlorinated paraffins, zinc dialkyldithiophosphates, zinc diaryldithiophosphates, dialkyldithiophosphate esters, diaryl dithiophosphate esters, phosphosulfurized hydrocarbons, and the like. Representative examples of such additives are those commercially available from The Lubrizol Corporation such as Lubrizol 677A, Lubrizol 1095, Lubrizol 1097, Lubrizol 1360, Lubrizol 1395, Lubrizol 5139, Lubrizol 5604 and the like, and from Ciba Corporation such as Irgalube 353 and the like.

Examples of friction modifiers include fatty acid esters and amides, organo molybdenum compounds, molybdenum dialkyldithiocarbamates, molybdenum dialkyl dithiophosphates, molybdenum disulfide, tri-molybdenum cluster dialkyldithiocarbamates, non-sulfur molybdenum compounds and the like. Representative examples of such friction modifiers are those commercially available from R.T. Vanderbilt Company, Inc. such as Molyvan A, Molyvan L, Molyvan 807, Molyvan 856B, Molyvan 822, Molyvan 855, and the like; Asahi Denka Kogyo K.K. such as SAKURA-LUBE 100, SAKURA-LUBE 165, SAKURA-LUBE 300, SAKURA-LUBE 310G, SAKURA-LUBE 321, SAKURA-LUBE 474, SAKURA-LUBE 600, SAKURA-LUBE 700, and the like;

and from Akzo Nobel Chemicals GmbH such as Ketjen-Ox 77M, Ketjen-Ox 77TS, and the like.

An example of an anti-foam agent is polysiloxane, and the like. Examples of rust inhibitors are polyoxyalkylene polyol, benzotriazole derivatives, and the like. Examples of VI improvers include olefin copolymers and dispersant olefin copolymers, and the like. An example of a pour point depressant is polymethacrylate, and the like.

As noted above, suitable anti-wear compounds include dihydrocarbyl dithiophosphates. Preferably, the hydrocarbyl groups contain an average of at least 3 carbon atoms. Particularly useful are metal salts of at least one dihydrocarbyl dithiophosphoric acid wherein the hydrocarbyl groups contain an average of at least 3 carbon atoms. The acids from which the dihydrocarbyl dithiophosphates can be derived can be illustrated by acids of the general formula:

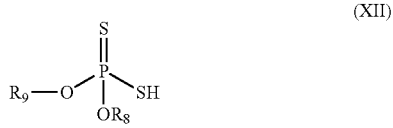

(XII)

wherein $R_8$ and $R_9$ are the same or different and can be linear or branched alkyl, cycloalkyl, aralkyl, alkaryl, or substituted substantially hydrocarbyl radical derivatives of any of the above groups, and wherein the $R_8$ and $R_9$ groups in the acid each have, on average, at least 3 carbon atoms. By "substantially hydrocarbyl" is meant radicals containing substituent groups, e.g., 1 to 4 substituent groups per radical moiety such as, for example, ether, ester, thio, nitro, or halogen, that do not materially affect the hydrocarbon character of the radical.

Specific examples of suitable $R_8$ and $R_9$ radicals include isopropyl, isobutyl, n-butyl, sec-butyl, n-hexyl, heptyl, 2-ethylhexyl, diisobutyl, isooctyl, decyl, dodecyl, tetradecyl, hexadecyl, octadecyl, butylphenyl, o,p-dipentylphenyl, octylphenyl, polyisobutene-(molecular weight 350)-substituted phenyl, tetrapropylene-substituted phenyl, beta-octylbutylnaphthyl, cyclopentyl, cyclohexyl, phenyl, chlorophenyl, o-dichlorophenyl, bromophenyl, naphthenyl, 2-methylcyclohexyl, benzyl, chlorobenzyl, chloropentyl, dichlorophenyl, nitrophenyl, dichlorodecyl and xenyl radicals. Alkyl radicals having from about 3 to about 30 carbon atoms and aryl radicals having from about 6 to about 30 carbon atoms are preferred. Particularly preferred $R_8$ and $R_9$ radicals are alkyl of from 4 to about 18 carbon atoms.

The phosphorodithioic acids are readily obtainable by the reaction of a phosphorus pentasulfide and an aliphatic alcohol and/or phenol. The reaction involves at least mixing, at a temperature ranging from about 20° C. to 200° C., about 4 moles of the alcohol or phenol with one mole of phosphorus pentasulfide. Hydrogen sulfide can be liberated as the reaction takes place. Mixtures of alcohols, phenols, or both can be employed, e.g., mixtures of $C_3$ to $C_{30}$ alcohols, $C_6$ to $C_{30}$ aromatic alcohols, etc. The metals useful to make the phosphate salts include, but are not limited to, Group I metals, Group II metals, aluminum, lead, tin, molybdenum, manganese, cobalt, and nickel with zinc being the preferred metal. Examples of metal compounds that can be reacted with the acid include lithium oxide, lithium hydroxide, lithium carbonate, lithium pentylate, sodium oxide, sodium hydroxide, sodium carbonate, sodium methylate, sodium propylate, sodium phenoxide, potassium oxide, potassium hydroxide, potassium carbonate, potassium methylate, silver oxide, silver carbonate, magnesium oxide, magnesium hydroxide, magnesium carbonate, magnesium ethylate, magnesium propylate, magnesium phenoxide, calcium oxide, calcium hydroxide, calcium carbonate, calcium methylate, calcium propylate, calcium pentylate, zinc oxide, zinc hydroxide, zinc carbonate, zinc propylate, strontium oxide, strontium hydroxide, cadmium oxide, cadmium hydroxide, cadmium carbonate, cadmium ethylate, barium oxide, barium hydroxide, barium hydrate, barium carbonate, barium ethylate, barium pentylate, aluminum oxide, aluminum propylate, lead oxide, lead hydroxide, lead carbonate, tin oxide, tin butylate, cobalt oxide, cobalt hydroxide, cobalt carbonate, cobalt pentylate, nickel oxide, nickel hydroxide, nickel carbonate and the like and mixtures thereof.

In some instances, the incorporation of certain ingredients, particularly carboxylic acids or metal carboxylates, e.g., small amounts of the metal acetate or acetic acid, used in conjunction with the metal reactant will facilitate the reaction and result in an improved product. For example, the use of up to about 5% of zinc acetate in combination with the required amount of zinc oxide facilitates the formation of a zinc phosphorodithioate.

The preparation of metal phosphorodithioates is well known in the art. See, e.g., U.S. Pat. Nos. 3,293,181; 3,397,145; 3,396,109; and 3,442,804; the disclosures of which are hereby incorporated by reference. Also useful as anti-wear additives are amine derivatives of dithiophosphoric acid compounds, such as are described in U.S. Pat. No. 3,637,499, the disclosure of which is hereby incorporated by reference in its entirety.

The zinc salts are most commonly used as anti-wear additives in lubricating oils in amounts ranging from about 0.1 to about 10, preferably about 0.2 to about 2 wt. %, based upon the total weight of the lubricating oil composition. They may be prepared in accordance with known techniques, e.g., by first forming a dithiophosphoric acid, usually by reaction of an alcohol and/or a phenol with $P_2S_5$ and then neutralizing the dithiophosphoric acid with a suitable zinc compound.

Mixtures of alcohols can be used, including mixtures of primary and secondary alcohols, secondary generally for imparting improved antiwear properties and primary for thermal stability. In general, any basic or neutral zinc compound could be used, but the oxides, hydroxides, and carbonates are most generally employed. Commercial additives frequently contain an excess of zinc owing to use of an excess of the basic zinc compound in the neutralization reaction.

The zinc dihydrocarbyl dithiophosphates (ZDDP) are oil soluble salts of dihydrocarbyl esters of dithiophosphoric acids and can be represented by the following general formula:

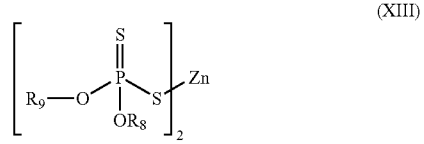

(XIII)

wherein $R_8$ and $R_9$ have the aforestated meanings.

The lubricating oil compositions of the present invention, when they contain these additives, are typically blended into a base oil in amounts such that the additives therein are effective to provide their normal attendant functions. Representative effective amounts of such additives are illustrated in Table 1.

TABLE 1

| Additives | Preferred Weight % | More Preferred Weight % |
|---|---|---|
| V.I. Improver | about 1 to about 12 | about 1 to about 4 |
| Corrosion Inhibitor | about 0.01 to about 3 | about 0.01 to about 1.5 |
| Oxidation Inhibitor | about 0.01 to about 5 | about 0.01 to about 1.5 |
| Dispersant | about 0.1 to about 10 | about 0.1 to about 5 |
| Lube Oil Flow Improver | about 0.01 to about 2 | about 0.01 to about 1.5 |
| Detergent/Rust Inhibitor | about 0.01 to about 6 | about 0.01 to about 3 |
| Pour Point Depressant | about 0.01 to about 1.5 | about 0.01 to about 0.5 |
| Anti-foaming Agents | about 0.001 to about 0.1 | about 0.001 to about 0.01 |
| Anti-wear Agents | about 0.001 to about 5 | about 0.001 to about 1.5 |
| Seal Swell Agents | about 0.1 to about 8 | about 0.1 to about 4 |
| Friction Modifiers | about 0.01 to about 3 | about 0.01 to about 1.5 |
| Lubricating Base Oil | Balance | Balance |

When other additives are employed, it may be desirable, although not necessary, to prepare additive concentrates comprising concentrated solutions or dispersions of the diaromatic amine derived additives of this invention (in concentrate amounts described herein), together with one or more other additives (the concentrate when constituting an additive mixture being referred to herein as an additive-package) whereby several additives can be added simultaneously to the base oil to form the lubricating oil composition. Dissolution of the additive concentrate into the lubricating oil can be facilitated by, for example, solvents and by mixing accompanied by mild heating, but this is not essential. The concentrate or additive-package will typically be formulated to contain the additives in proper amounts to provide the desired concentration in the final formulation when the additive-package is combined with a predetermined amount of base lubricant. Thus, the diaromatic amine derived additives of the present invention can be added to small amounts of base oil or other compatible solvents along with other desirable additives to form additive-packages containing active ingredients in collective amounts of, typically, from about 2.5 to about 90 percent, preferably from about 15 to about 75 percent, and more preferably from about 25 percent to about 60 percent by weight additives in the appropriate proportions with the remainder being base oil. The final formulations can typically employ about 1 to 20 weight percent of the additive-package with the remainder being base oil.

All of the weight percentages expressed herein (unless otherwise indicated) are based on the active ingredient (AI) content of the additive, and/or upon the total weight of any additive-package, or formulation, which will be the sum of the AI weight of each additive plus the weight of total oil or diluent. In general, the lubricant compositions of the invention contain the additives in a concentration ranging from about 0.05 to about 30 weight percent. A concentration range for the additives ranging from about 0.1 to about 10 weight percent based on the total weight of the oil composition is preferred. A more preferred concentration range is from about 0.2 to about 5 weight percent. Oil concentrates of the additives can contain from about 1 to about 75 weight percent of the additive in a carrier or diluent oil of lubricating oil viscosity.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

EXAMPLES

The following examples illustrate the many advantages of the compounds according to the present invention.

Example 1

A mixture of the 2-aminoindan (39.8 g, 300 mmol), 2-bromoindan (65 g, 329 mol) and 50% NaOH (22 mL) in toluene (220 mL) was purged with nitrogen for 45 minutes. Bis(tri-t-butylphosphine)palladium(0) (1.6 g, 3.2 mmol) and cetyltrimethylammonium bromide (0.56 g, 1.6 mmol) were added to the flask under a stream of nitrogen. The mixture was then heated at about 100° C. for four days and then left to cool overnight without stirring. The mixture was filtered through Celite and the filter cake rinsed with toluene. The solution was extracted with water (100 mL) and concentrated through vacuum distillation. The resulting residue was distilled on a short-path Kugelrohr apparatus with a vacuum. A forerun fraction was collected up to 140° C. at 0.89 T. After further heating to 160° C. (at 0.6-3.6 T), the product (73 g, 97% yield) was distilled as a light yellowish oil which solidified on standing. GC/FID analysis indicated a purity of 99% (by area %). The product was further recrystallized in hexanes to give colorless solid. This reaction is generally shown below in Scheme I.

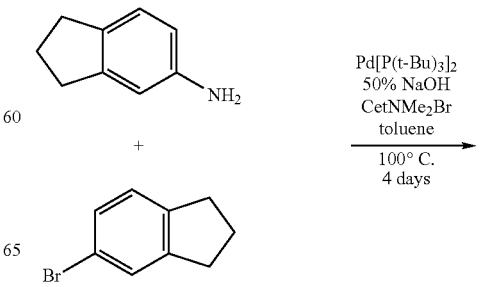

Scheme I

-continued

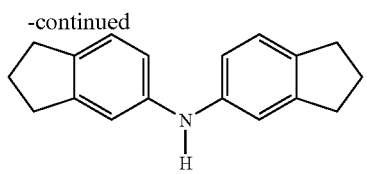

The resulting β,β-diindanamine had an empirical formula of $C_{18}H_{19}N$ and an average weight molecular weight of 249.36. The yield was 73 g, 97%.

β,β-diindanamine (4.40 gram, 17.65 mmol, 1.00 eq.) was added under ambient condition to a 250 mL round bottom flask followed by allylbromide (2.56 gram, 21.17 mmol, 1.20 eq.), potassium carbonate (3 gram), and DMSO (10 mL). The reaction is exothermic, and after 4 hrs, the mixture was poured into 100 mL water, and extracted with 100 mL hexane twice, and the organic phase was washed with water (100 mL, twice). The organic phase was then dried over anhydrous $MgSO_4$, and all the solvent was removed via vacuum distillation to give product as light yellowish liquid. This reaction is generally shown below in Scheme II.

Scheme II

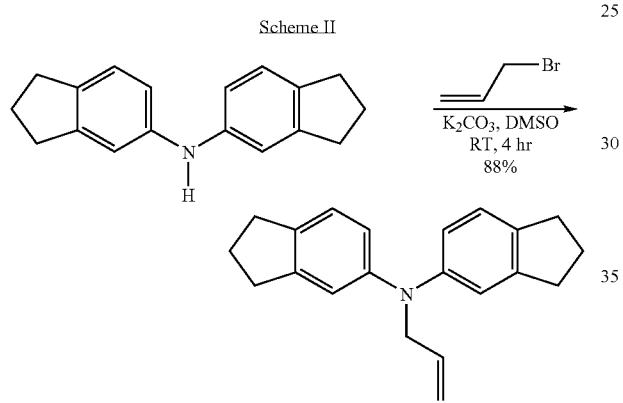

The resulting diaromatic amine derivative compound had an empirical formula of $C_{21}H_{23}N$ and an average weight molecular weight of 289.42. The yield was 4.5 g, 88%. $^1$H NMR (CDCl$_3$) δ=7.12 (2H, d, J=6.8 Hz), 6.88 (2H, s), 6.84 (2H, d, J=6.8 Hz), 5.96 (1H, m), 5.30 (1H, d, J=17.4 Hz), 5.18 (1H, d, J=8.7 Hz), 4.34 (2H, s), 2.88 (8H, s), 2.08 (4H, m) ppm. $^{13}$C NMR (CDCl$_3$) δ=147.00 (s), 145.29 (d), 136.74 (d), 134.85 (s), 124.62 (d), 118.91 (d), 116.88 (d), 116.02 (s), 55.33 (t), 33.09 (t), 32.14 (t), 25.65 (t) ppm.

Example 2

To a motor oil formulation was blended 1 weight percent of the diaromatic amine derivative Example 1 to form a SAE 10W-30 motor oil formulation. The SAE 10W-30 motor oil formulation is set forth in Table 2.

TABLE 2

| SAE 10W-30 Motor Oil Formulation (Base Blend) | |
|---|---|
| | wt % |
| Solvent Neutral 100 | Balance |
| Overbased Calcium Sulfonate Detergent | 1.3 |
| Rust/Corrosion Inhibitor | 0.75 |
| Commercial or experimental Antioxidant | 1.0 |

TABLE 2-continued

| SAE 10W-30 Motor Oil Formulation (Base Blend) | |
|---|---|
| | wt % |
| Pour Point Depressant | 0.1 |
| OCP VI Improver | 5.5 |
| ZDDP | 0.8 |

Comparative Example A

Preparation of SAE 10W-30 Motor Oil Formulation

The SAE 10W-30 motor oil formulation set forth in Table 2 was prepared with no antioxidant added of any type.

Comparative Example B

Preparation of SAE 10W-30 Motor Oil Formulation

To the SAE 10W-30 motor oil formulation set forth in Table 2 was blended 1 weight percent of alkylated diphenyl amine (commercially available as Naugalube 438L). Naugalube 438L is a complex mixtures of $C_9$ olefin alkylated diphenylamine (DPA), including mono-$C_9$ alkylated DPA, di-$C_9$ alkylated DPA, and some tri-$C_9$ alkylated DPA, as shown in general formula:

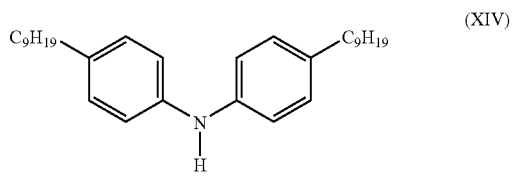

(XIV)

Example 3

Mid-High Temperature Thermo-Oxidative Engine Oil Simulation Test

The Mid-High Temperature Thermo-oxidative Engine Oil Simulation Test (TEOST MHT®, ASTM D 7097, the entirety of which is incorporated herein by reference) was performed to determine the deposit forming tendencies of the motor engine oil. The improved thermal deposit control of the additives of this invention in stabilizing the engine oil formulation has been clearly demonstrated by the MHT TEOST. This test determines the mass of deposit formed on a specially constructed steel rod by continuously stressing a repetitive passage of 8.5 ml of test oil under thermal-oxidative and catalytic conditions. The instrument used was manufactured by Tannas Co. and has a typical repeatability of 0.15 (x+16) mg wherein x is the mean of two or more repeated test results. The TEOST test conditions are listed in Table 3. The less the amount of deposits obtained, the better the oxidation stability of the oil. The results of this test are set forth in Table 4.

TABLE 3

| TEOST MHT Test Conditions | |
|---|---|
| Test Parameters | Settings |
| Test duration | 24 hours |
| Rod Temperature | 285° C. |
| Sample size | 8.5 g (mixture of 8.4 g of oil and 0.1 g of catalyst) |
| Sample flow rate | 0.25 g/min |
| Flow rate (dry air) | 10 mL/min |
| Catalyst | Oil soluble mixture containing Fe, Pb, and Sn |

TABLE 4

| TEOST Results | |
|---|---|
| Ex./Comp. Ex. | mg deposits |
| Example 2 | 23.2 |
| Comp. Ex. A | 108.0 |
| Comp. Ex. B | 71.2 |

It can be seen from the above data that the addition of a compound produced from example 1 to a lubricating oil composition in examples 2 and 3 significantly reduces the total deposit mass of the base blend formulation.

What is claimed is:

1. A diaromatic amine compound having the general formula:

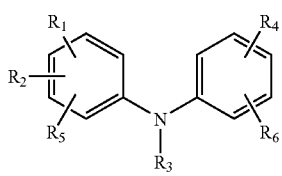

wherein $R_1$ and $R_2$ together with the carbon atoms to which they are bonded are joined together to form a first $C_3$-$C_{30}$ ring;
$R_3$ is an allyl, benzyl, or methallyl group;
$R_4$ and $R_6$ together with the carbon atoms to which the are bonded are joined together to form a second $C_3$-$C_{30}$ ring; and
$R_5$ is hydrogen, substituted or unsubstituted $C_1$-$C_{30}$ alkyl group, substituted or unsubstituted $C_2$-$C_{30}$ alkenyl group, substituted or unsubstituted $C_3$-$C_{12}$ cycloalkyl group, substituted or unsubstituted $C_5$-$C_{25}$ aryl group, $C_6$-$C_{25}$ arylalkyl group, or $C_1$-$C_{30}$ alkoxy group.

2. The compound of claim 1, where any of the $C_3$-$C_{30}$ rings, $C_1$-$C_{30}$ alkyl group, $C_2$-$C_{30}$ alkenyl group, $C_3$-$C_{12}$ cycloalkyl group, $C_5$-$C_{25}$ aryl group, $C_6$-$C_{25}$ arylalkyl group, or $C_1$-$C_{30}$ alkoxy group is substituted with one or more substituents, the substituents are selected from hydroxy, halogen, carboxyl, cyano, nitro, oxo, thio, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted or unsubstituted heterocycloalkyl ring, substituted or unsubstituted heteroarylalkyl, substituted or unsubstituted heterocyclic ring, —COOR$_x$, —C(O)NR$_x$R$_y$, —NR$_x$R$_x$, C(O)R$_x$, —OR$_x$, —OC(O)R$_x$, —OC(O)NR$_x$R$_x$, —SR$_x$, —SOR$_x$, —SO$_2$R$_x$, wherein R$_x$ and R$_x$ in each comprises a saturated or unsaturated chain of 1 to 30 carbons.

3. The compound of claim 1, wherein $R_1$ and $R_2$ are joined together to form a saturated 5-, 6- or 7-membered ring.

4. The compound of claim 1, wherein $R_1$ and $R_2$ are joined together to form a partially unsaturated or fully unsaturated 5-, 6- or 7-membered ring.

5. The compound of claim 1 of general formula:

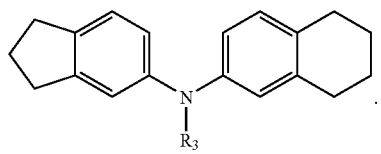

6. The compound of claim 1 of general formula:

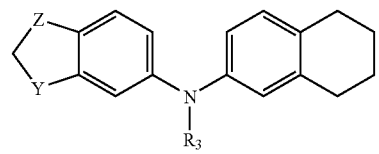

wherein Z and Y are heteroatoms.

7. The compound of claim of general formula:

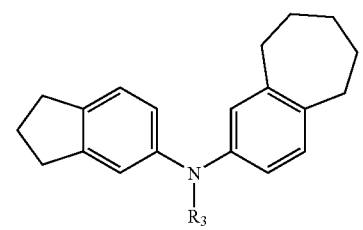

8. The compound of claim of the formula:

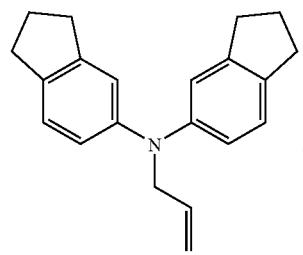

9. A lubricating oil composition comprising:
at least one oil of lubricating viscosity; and
an antioxidant improving effective amount of at least one diaromatic amine compound having the general formula of claim 1.

10. The lubricating oil composition of claim 9, wherein the at least one oil of lubricating viscosity is selected from the group consisting of engine oils, transmission fluids, hydraulic fluids, gear oils, marine cylinder oils, compressor oils, refrigeration lubricants and mixtures thereof.

11. The lubricating oil composition of claim 9, further comprising at least one lubricating oil additive selected from the group consisting of antioxidants, anti-wear agents, detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and mixtures thereof.

12. The lubricating oil composition of claim 11, wherein the lubricating oil composition with the at least one lubricating oil additive has a phosphorous content of less than about 0.1 weight percent.

13. The lubricating oil composition of claim 9, further comprising at least one lubricating oil additive selected from the group consisting of an alkylated diphenylamine, alkylated hindered phenolic, alkylated substituted or unsubstituted phenylenediamine, alkylated oil soluble copper compound, alkylated sulfur containing compound known to impart oxidation stability and mixtures thereof.

14. The lubricating oil composition of claim 13, wherein the alkylated sulfur containing compound known to impart oxidation stability is selected from the group consisting of phenothiazines, sulfurized olefins, thiocarbamates, sulfur bearing hindered phenolics, zinc dialkyldithiophosphates and mixtures thereof.

15. An additive package comprising about 0.1 to about 75 weight percent of at least one diaromatic amine compound having the general formula of claim 1.

16. A stabilizer-containing composition comprising:
(a) an organic material subject to oxidative, thermal, and/or light-induced degradation and in need of stabilization to prevent or inhibit such degradation; and
(b) a stabilization effective amount of at least one diaromatic amine compound having the general formula of claim 1.

17. A method for stabilizing an organic material subject to oxidative, thermal, and/or light-induced degradation and in need of stabilization to prevent or inhibit such degradation, the method comprising adding to the organic material a stabilizing amount of at least one diaromatic amine compound having the general formula of claim 1.

18. A compound comprising:
a diaromatic amine having at least two phenyl groups bonded to a nitrogen, wherein the nitrogen is further bonded to a carbon containing substituent group such that the compound is incapable of being an electron withdrawing group;
a first ring fused to one of the phenyl groups; and
further comprising a second ring fused to one of the other phenyl groups.

* * * * *